(12) United States Patent
Esteban Duran

(10) Patent No.: US 6,513,726 B1
(45) Date of Patent: Feb. 4, 2003

(54) PROCESS AND DEVICES FOR THE CONSTANT EMISSION OF VOLATILE LIQUIDS

(75) Inventor: José Rafael Esteban Duran, Madrid (ES)

(73) Assignee: Instituto Nacional De Investigacion Y Tecnologia Agraria Y Alimentaria, Madrid (ES)

( * ) Notice: Subject to any disclaimer, the term of this patent is extended or adjusted under 35 U.S.C. 154(b) by 0 days.

(21) Appl. No.: 09/142,044
(22) PCT Filed: Jan. 19, 1998
(86) PCT No.: PCT/ES98/00009
§ 371 (c)(1), (2), (4) Date: Sep. 16, 1998
(87) PCT Pub. No.: WO98/31401
PCT Pub. Date: Jul. 23, 1998

(30) Foreign Application Priority Data

Jan. 20, 1997 (ES) .................................. 9700101

(51) Int. Cl.[7] .............................................. A61L 9/08
(52) U.S. Cl. ......................................................... 239/44
(58) Field of Search ..................................... 239/44–49

(56) References Cited

U.S. PATENT DOCUMENTS

| 2,723,158 | A | * | 11/1955 | Molina ......................... 239/44 |
| 4,621,768 | A | | 11/1986 | Lhoste et al. |
| 4,915,301 | A | | 4/1990 | Munteanu |
| 5,000,383 | A | * | 3/1991 | Van Der Heijden .......... 239/44 |
| 5,603,455 | A | * | 2/1997 | Lin ............................... 239/44 |

FOREIGN PATENT DOCUMENTS

| EP | 134360 | 3/1985 |
| FR | 2653979 | 5/1991 |

* cited by examiner

Primary Examiner—Steven O. Douglas
(74) Attorney, Agent, or Firm—Ostrolenk, Faber, Gerb & Soffen, LLP

(57) ABSTRACT

A process for the constant emission of volatile products in the liquid state, which may be either natural or synthetic products or compounds (with or without solutes), uses solid absorbent masses of different materials of a diverse nature and composition. A specifically designed and mutually mechanically linked device forming a homogenous set is used for effectively achieving this process.

4 Claims, 2 Drawing Sheets

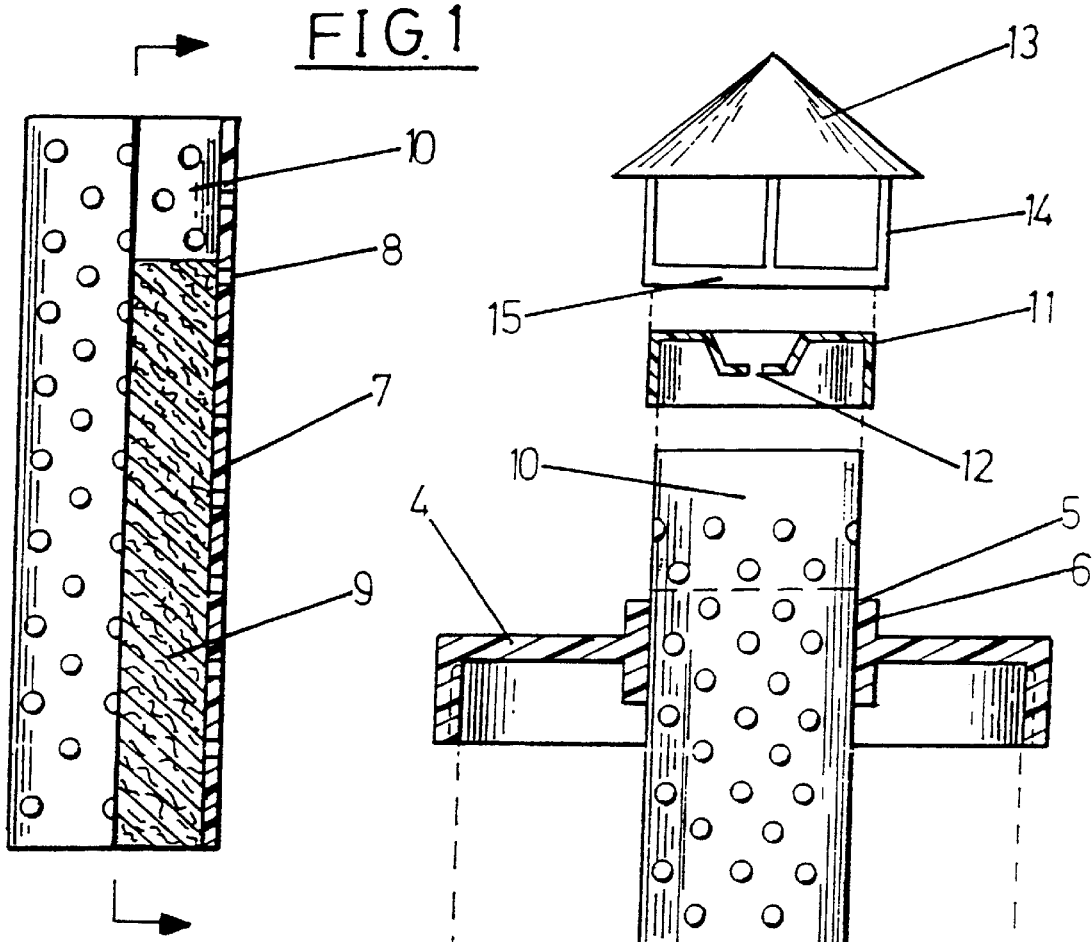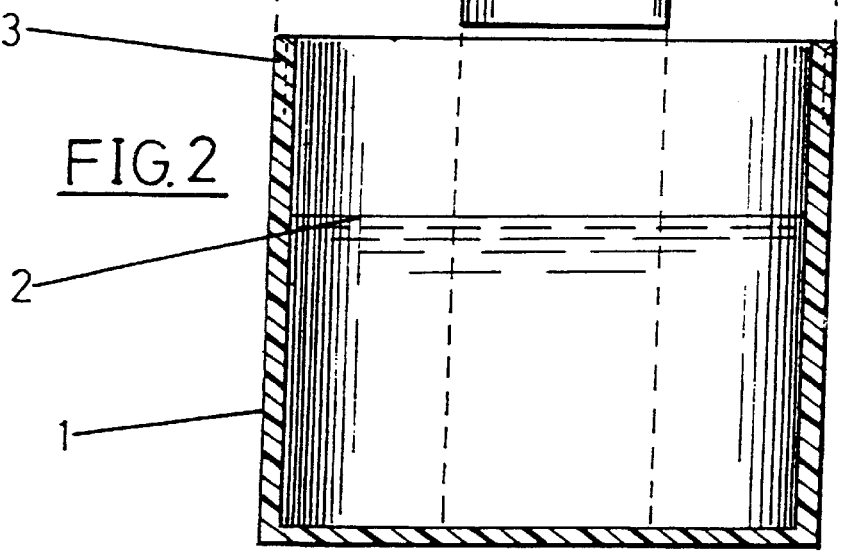

PROCESS AND DEVICES FOR THE CONSTANT EMISSION OF VOLATILE LIQUIDS

OBJECT OF THE INVENTION

The object of the invention, as the name implies, is a "process and device for the constant emission of volatile liquids".

The process proposed by the invention is based on the absorption of liquids and/or volatile solvents (with or without accompanying solutes) through solid absorbents made of diverse materials of a different nature and composition.

BACKGROUND OF THE INVENTION

At present, volatile liquid products such as insecticides, aromatic substances, disinfectants, phytosanitary products, semochemicals, etc., are dispersed with the use of dispersing products or generally manual, mechanical, thermoelectrical or otherwise activated devices requiring continuous attention which in many cases renders their use impracticable. On the other hand, these dispersing devices fail to provide a constant emission of the volatile product in question.

In specific cases where the product must be dispersed over extended areas of farm or woodland, applying these products requires a large number of special machines and propellents which are almost impossible to install, particularly in places that are not readily accessible.

Known dispersers of a scientific nature based on fluid mechanics or physics fail to provide satisfactory results in equatorial or tropical environments with extremely high diurnal temperatures, high levels of relative humidity, abrupt temperature falls during the dusk and night hours and ambient humidities in the order of 100%.

On the other hand, the use of additional driving elements of a mechanical or thermoelectrical nature which could (and in some cases do) solve this problem entails high operating costs and the difficulty of reaching almost inaccessible locations lacking electricity or fuel for driving the system.

The invention presents a simple and efficient solution to these problems and proposes the process and special device described hereunder.

The use of dispersers heretofore available in the market and applied to agricultural and forestry research purposes in moderate continental climates presents several practical inconveniences which may be overcome by manual modifications varying from one case to the other. However, the use of known dispersers in wet equatorial forest environments fails to respond to the minimum expected operational requirements.

Bearing in mind that the research undertaken employed dispersers that were calibrated to some extent, solving the problems encountered in the putting into operation as a result of basic instrument failures was the first step toward executing the work.

As a first step, a thorough examination was carried out to establish the causes that led to known disperser failures essentially deriving from the critical ambient temperature and humidity conditions that prevailed, particularly in the Amazon forest. During diurnal hours, with a constant temperature of 30° C. and a relative humidity never under 85%, dispersion of the volatile liquids took place at an extremely high (evaporated volume/time unit) rate. On the contrary, as from dusk, when the relative humidity reached 100% (condensation), the temperature dropped to under 18° C. and the condensation water created a tight chamber around the disperser which fully inhibited the evaporation of the volatile liquid to be dispersed.

Since the causes of known disperser failures could not be solved by modifying the dispersers, other devices had to be created.

A disperser was thus created which is capable of efficiently responding to the required demands.

The results obtained, which solve the problem involving a break in the dispersion caused by a relative humidity of almost 100%, in addition to continuous and regular daily dispersion rates which varied from 0.5 to more than 2 cc, led to the creation of the system proposed in this document.

It should be understood that the invention has multiple sanitary, cosmetic, agricultural, forestry, etc., applications.

DESCRIPTION OF THE INVENTION

In the process described, absorption of the liquids and/or volatile solvents (with or without accompanying solutes) is conducted through solid absorbents from which they emanate in the form of gas by a physical principle involving vapor pressure differences and air drawing, without the weight of the liquid or solvent intervening and resorting neither to motor and thermoelectrical means nor to compressed fluid dispersers.

Through the process advocated by the invention, constant dispersion of the substances is achieved in a free or controlled manner, depending on the selected option.

The following elements are foreseen for putting the described process to practical use:

a) A tank containing the liquid product or composition to be dispersed.

b) An absorbent-diffuser mass, duly conditioned and protected, contained in the above tank and totally or partially immersed in the liquid product to be dispersed.

c) A tubular body, with multiple strategically distributed holes, for holding the absorbent mass.

d) A perpendicular tube or sleeve either incorporated or integral to the tank's closing lid, said sleeve having the absorbent mass-containing tubular body tightly adapted thereto in such a way that the mass is immersed in the liquid in the tank.

e) A tank closing lid providing a virtually impervious closure, said lid sustaining the perforated tubular element in an upright position, from the upper end of which flows, in its gaseous state, the liquid product contained in the tank.

f) The perforated tubular body holding the absorbent mass is free of absorbent material in its upper portion, which forms a chamber with unobstructed holes allowing the external gas-carrying air to flow therethrough, into the chamber and on to the outlet passage.

g) A disk-shaped, centrally perforated lid which tightly adapts to the upper end of the perforated tubular body and closes the chamber formed in said body.

h) A roof-shaped lid which closes the free upper end of the device and furthermore covers and protects the outlet passage of the product in its gaseous state, avoiding obstructions.

The following description provides a better understanding of the object of the invention if contemplated jointly with the attached drawings that show, somewhat schematically and purely in the form of a non-limiting example, the preferred assemblies and details of the devices for a practical embodiment of said object of the invention.

In the drawings:

FIG. 1 shows a half-section elevational view along a vertical plane of the perforated tubular element holding the absorbent mass.

FIG. 2 shows an exploded view of the set of elements comprising the overall liquid product emission device.

Figure 3:
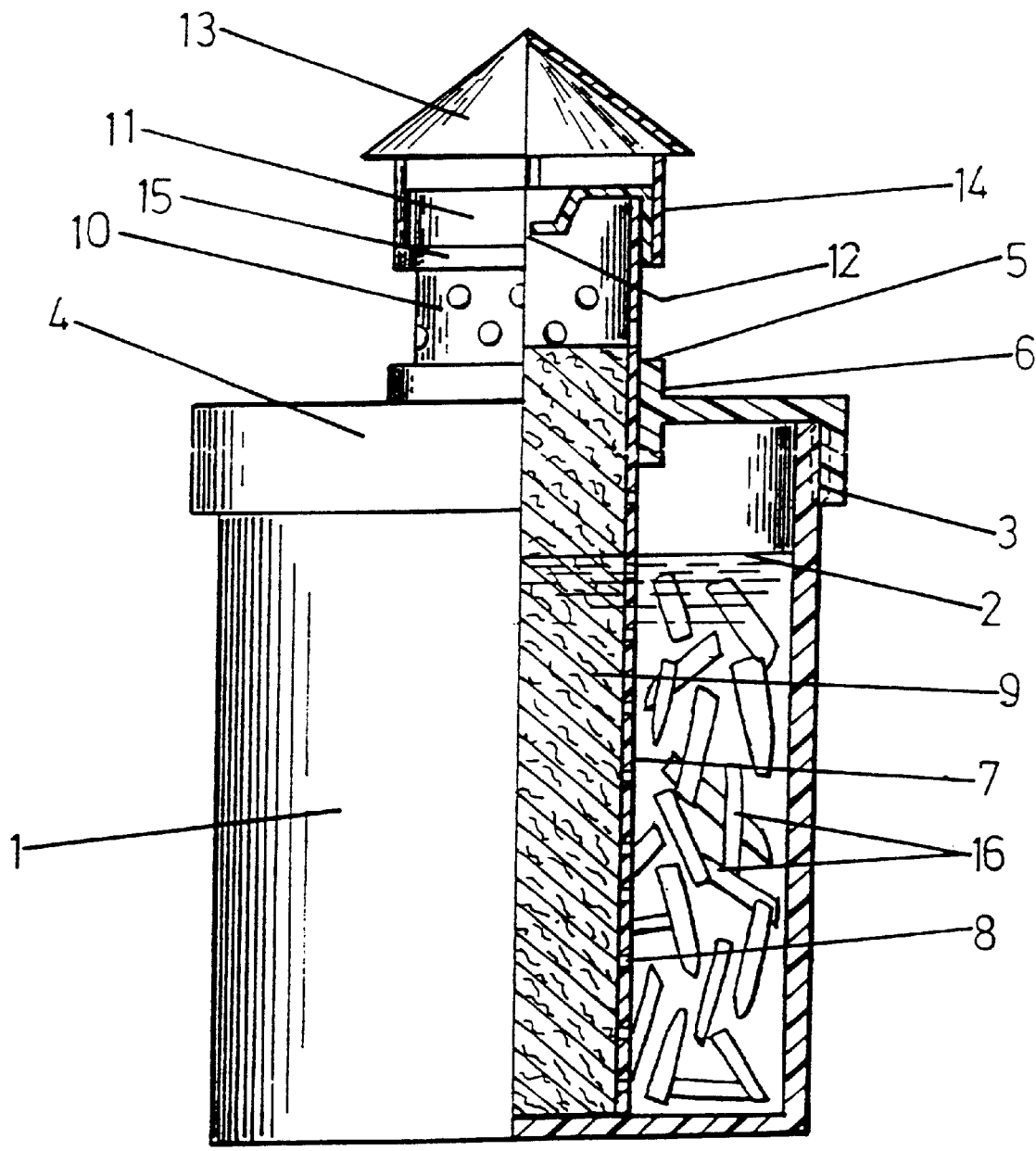
FIG. 3 shows a half-section elevational view along a vertical plane of the grouped set of elements forming the disperser, depicted in a fully assembled manner, its tank containing the liquid product to be dispersed.

Commenting on the drawings, reference number 1 identifies the tank containing the liquid product, the level of which is identified by reference number 2. In the practical embodiment of the invention, this tank forms a vessel fitted with means 3 for receiving and securely retaining a disk-shaped lid 4 providing a virtually impervious closure; said lid 4 is fitted with a large central hole 5 surrounded by a neck 6 extending from both top and bottom surfaces of lid 4 to define the central hole 5 and to form a tubular housing for tightly holding a tubular cylindrical element 7 endowed with strategically distributed holes 8 throughout its surface. The tubular element 7 contains an absorbent mass 9; said tubular element 7 penetrates perpendicularly in the tank 1, rests on the bottom thereof in a securely upright position and protrudes above the lid 4 along a portion devoid of absorbent mass. This free portion forms a chamber 10 into which ambient air penetrates through the holes 8 to displace the gases emitted from the absorbent mass, causing the emitted gases to flow through a passage 12 located at the center of a closing part 11 tightly fitted onto the upper end of tubular element 7. Lastly, the closure part 11 is covered by a bonnet 13 supported by support elements 14 which extend from an annular sector of base 15 fitted over the closing part 11 providing the upper closure of perforated tube 7.

The tank 1 holds the liquid product or composition 2, which may additionally contain other finely divided or solid components, as indicated by reference number 16.

Following its preparation, the liquid product or composition to be dispersed is fed into the tank 1 up to a specified level 2, optionally incorporating solid or powdered components 16. The tubular body 7 formed with holes 8 and containing the absorbent mass 9 is inserted perpendicularly in an upright position and is immersed in the liquid which, through the holes 8, impregnates the overall absorbent mass 9. Upon impregnating the absorbent mass 9, the liquid then flows in its gaseous state into the upper chamber 10, from where it is conveyed to passage 12 by the air entering the chamber 10 formed in the upper end of the perforated tubular body 7, to be finally dispersed in the external environment. Over the upper end of tubular body 7 and closing part 11 is installed a covering element formed by a substantially conical bonnet 13 supported by vertical supports 14 which extend from an annular base 15 securely fitted over the lid 11 which closes the upper end of central body 7.

The nature of the invention being thus conveniently described, it should be stated that the effects of the invention are not strictly limited to the exact details of this description, so that, upon embodiment, modifications to these details may be introduced provided the resulting variations do not alter the essence of the invention.

What is claimed is:

1. A device for the constant emission of volatile liquids comprising:

a tank having a bottom and containing a volatile liquid product to be dispersed;

an absorbent mass for absorbing the product to be dispersed;

a tubular body having a plurality of holes formed around and along the surface thereof, an upper end, a lower end, and an interior volume, the tubular body arranged in a vertical position wherein the lower end of the tubular body rests on the bottom of the tank, wherein the absorbent mass fills the interior volume of the tubular body except at the upper end of the tubular body, the interior volume at the upper end of the tubular body which is devoid of the absorbent mass forming a chamber, and wherein the absorbent mass is in contact with the liquid product contained in the tank through the plurality of holes in the tubular body;

a tank closure lid provided with a central hole having a diameter which allows the tubular body to be passed therethrough; and a tubular body closing element provided with a central opening, the tubular body closing element being tightly fitted on the upper end of the tubular body such that the product to be dispersed is capable of flowing, in the form of a gas, through the central opening for dispersion.

2. A device according to claim 1, wherein the chamber devoid of the absorbent mass at the upper end of the tubular body protrudes above said tank closure lid, such that air can penetrate into said chamber through the plurality of holes at the upper end of the tubular body so that the product which flows in the form of a gas from the absorbent mass into the chamber is caused to flow through the central opening and out of the device.

3. A device according to claim 1, further comprising a covering element disposed above the upper end of the tubular body and the tubular body closing element, the covering element being shaped as a bonnet having a diameter bigger than the diameter of the tubular body closing element for protecting the central opening from potential obstructions.

4. A device according to claim 1, wherein the liquid product includes a solid material in suspension.

* * * * *